US007182736B2

(12) United States Patent
Roy et al.

(10) Patent No.: US 7,182,736 B2
(45) Date of Patent: *Feb. 27, 2007

(54) APPARATUS AND METHOD FOR ASSESSING LOADS ON ADJACENT BONES

(75) Inventors: Shuvo Roy, Cleveland, OH (US); Aaron J. Fleischman, University Heights, OH (US); Edward C. Benzel, Gates Mills, OH (US); Lisa Ferrara, Cleveland Heights, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/769,823

(22) Filed: Feb. 2, 2004

(65) Prior Publication Data

US 2004/0186396 A1 Sep. 23, 2004

Related U.S. Application Data

(63) Continuation of application No. 09/939,331, filed on Aug. 24, 2001, now Pat. No. 6,706,005.

(60) Provisional application No. 60/228,166, filed on Aug. 25, 2000.

(51) Int. Cl.
*A61B 5/117* (2006.01)
*A61B 5/103* (2006.01)

(52) U.S. Cl. ...................................................... 600/587

(58) Field of Classification Search ................ 600/587, 600/594, 300; 435/174, 176, 177, 180, 181; 436/518, 524, 528, 531; 424/178.1; 530/402, 530/815, 810–812; 623/16, 17

See application file for complete search history.

(56) References Cited

U.S. PATENT DOCUMENTS 5,425,775 A 6/1995 Kovacevic et al.
5,456,724 A 10/1995 Yen et al.

(Continued)

OTHER PUBLICATIONS

IEEE Transactions on Biomedical Engineering, vol. 47, No. 1, Jan. 2000 “A Portable Microsystem-Based Telemetric Pressure and Temperature Measurement Unit”, Bernd B. Flick and Reinhold Orgimeister.

Med. Eng. Phys. vol. 19, No. 6, pp. 539-549, 1997 “Comparison of Loads on Internal Spinal Fixation Devices Measured in Vitro and in Vivo”, A. Rohlmann, G. Bergmann, F. Graichen and U. Weber.

(Continued)

*Primary Examiner*—Max F. Hindenburg
*Assistant Examiner*—Brian Szmal
(74) *Attorney, Agent, or Firm*—Tarolli, Sundheim, Covell & Tummino LLP

(57) ABSTRACT

An apparatus (10) that utilizes microelectromechanical systems (MEMS) technology to provide an in vivo assessment of loads on adjacent bones (24 and 26) comprises a body (34) for insertion between the adjacent bones. At least one sensor (42) is associated with the body (34). The sensor (42) generates an output signal in response to and indicative of a load being applied to the body (34) through the adjacent bones (24 and 26). A telemetric device (40) is operatively coupled with the sensor (42). The telemetric device (40) is operable to receive the output signal from the sensor (42) and to transmit an EMF signal dependent upon the output signal. According to various aspects of the invention, the sensor comprises a pressure sensor (42), a load cell (320), and/or at least one strain gauge (142).

13 Claims, 8 Drawing Sheets

142 128 132 210 146 220 148 26 240 34 140 24 142 144

U.S. PATENT DOCUMENTS

| | | | | |
|---|---|---|---|---|
| 5,470,354 | A | 11/1995 | Hershberger et al. | |
| 5,531,787 | A | 7/1996 | Lesinski et al. | |
| 5,843,082 | A | 12/1998 | Yuan et al. | |
| 5,925,552 | A * | 7/1999 | Keogh et al. | 435/174 |
| 6,034,296 | A | 3/2000 | Elvin et al. | |
| 6,036,693 | A | 3/2000 | Yuan et al. | |
| 6,059,784 | A | 5/2000 | Perusek | |
| 6,342,074 | B1 | 1/2002 | Simpson | |
| 6,447,448 | B1 | 9/2002 | Ishikawa et al. | |
| 6,706,005 | B2 * | 3/2004 | Roy et al. | 600/594 |
| 2002/0010390 | A1 * | 1/2002 | Guice et al. | 600/300 |

OTHER PUBLICATIONS

Journal of Microelectromechanical Systems, vol. 9, No. 1, Mar. 2000, A Miniature Pressure System With a Capacitive Sensor and a Passive Telemetry Link for Use in Implantable Applications, Stavros Chatzandroulis, Dimitris Tsoukalas and Peter A. Neukomm.

"Introduction to MEMS", M. Mehrehany and S. Roy.

Spine vol. 25, No. 20, pp. 2595-2600 "Real-Time in Vivo Loading in the Lumbar Spine" "Part 1. Interbody Implant: Load Cell Design and Preliminary Results", Eric H. Ledet, MS, Barton L. Sachs, MD, John B. Brunski, PhD, Charles E. Gatto, MD, and Peter S. Donzelli, PhD.

* cited by examiner

APPARATUS AND METHOD FOR ASSESSING LOADS ON ADJACENT BONES

RELATED APPLICATIONS

This application is a continuation of U.S. patent application Ser. No. 09/939,331, filed Aug. 24, 2001 now U.S. Pat. No. 6,706,005 which claims priority from U.S. Provisional Patent Application Ser. No. 60/228,166, filed on Aug. 25, 2000, the subject matter of which is incorporated herein by reference.

TECHNICAL FIELD

The present invention relates to an apparatus and method for assessing loads on adjacent bones, and is particularly directed to an apparatus and method for providing an in vivo assessment of loads on adjacent bones to be fused together.

BACKGROUND OF THE INVENTION

It is known to use surgical procedures to stabilize a fractured bone or repair a problematic interaction of adjacent bones. For example, spinal surgery is frequently performed to stabilize a problematic portion of the spine and relieve pain. Often, the vertebrae in the problematic portion of the spine are fused together with a bone graft in order to achieve the stabilization. Because the bone fusion takes time (six months or more on average), spinal implants (often referred to as fixation instrumentation), such as rods, clamps, and plates, are typically implanted and used to secure the vertebrae while the fusion of the bone graft takes place.

During the months while the arthrodesis is occurring, it is desirable to monitor the progress of the bony incorporation, or bone-ingrowth, of the graft. Known methods for examining the bony incorporation include radiographic evaluation, magnetic resonance imaging, and computerized tomography. All of these techniques provide a snapshot of the progress of the bony incorporation, but do not provide accurate, continuous, real-time information to the patient and physician. Without the ability to accurately and continuously assess the bony incorporation, pseudoarthrosis (non-healed bone fusion) may occur unbeknownst to the physician. Such pseudoarthrosis may cause post-operative pain for the patient and necessitate additional surgery. If the fusion progress could be assessed continuously or on-demand during the post-operative period by assessing the loads on the fixation instrumentation, it may be possible to appropriately time additional surgery or even avoid additional surgery.

In a related manner, it is also desirable to assess the biomechanical performance of implanted spinal fixation instrumentation during the post-operative period while bone fusion is occurring. Both in vitro and in vivo biomechanical testing of fixation instrumentation has been done in the past, but with limited success. Current in vitro testing of fixation instrumentation typically subjects cadaveric vertebrae and implantable instrumentation to various axial and torsional loading parameters on a hydraulic testing apparatus. Unfortunately, the use of non-living cadaveric tissue can introduce significant error into the test data.

Previous attempts at in vivo biomechanical testing of spinal fixation instrumentation have been done primarily using animals (quadrapeds), but some limited testing has been done with humans. In one of the in vivo human tests performed to date, sensors that were placed on the implanted spinal instrumentation utilized wires to carry data percutaneously (through the skin) from the sensors to a data monitoring unit outside the human body. The use of wires or other type of electrical or optical connection extending through the skin provides a significant risk of infection and is not suitable for long-term testing as there is a high risk of wire breakage.

Another problem encountered with the in vivo testing that has been done is failure of a sensor, such as a strain gauge, or the sensor wiring which has been known to break, corrode, or debond within four months of in vivo implantation. While attempts have been made to use telemetry to transmit data from sensors implanted in transcranial applications to an external monitoring device, a need exists for an implantable, telemetered sensor arrangement for spinal or other orthopedic applications that could survive a minimum of a year.

Microelectromechanical systems, or MEMS, refers to a class of miniature electromechanical components and systems that are fabricated using techniques originally used in the fabrication of microelectronics. MEMS devices, such as pressure sensors and strain gauges, manufactured using microfabrication and micromachining techniques can exhibit superior performance compared to their conventionally built counterparts and are resistant to failure due to corrosion, etc. Further, due to their extremely small size, MEMS devices can be utilized to perform functions in unique applications, such as the human body, that were not previously feasible using conventional devices.

SUMMARY OF THE INVENTION

The present invention is an apparatus for providing an in vivo assessment of loads on adjacent bones. The apparatus comprises a body for insertion between the adjacent bones. At least one sensor is associated with the body. The at least one sensor generates an output signal in response to and indicative of a load being applied to the body through the adjacent bones. At least one telemetric device is operatively coupled with the at least one sensor. The least one telemetric device is operable to receive the output signal from the at least one sensor and to transmit an electromagnetic field (EMF) signal dependent upon the output signal.

In accordance with one embodiment of the invention, the body comprises an implant for helping the adjacent bones to fuse together. The implant comprises a bone graft. In accordance with another embodiment of the invention, the body comprises a fusion cage for insertion between an adjacent pair of vertebrae. In accordance with yet another embodiment, the body comprises a prosthetic device for preserving motion between adjacent bones.

According to various features of the invention, the at least one sensor comprises a pressure sensor, a load cell, and/or at least one strain gauge.

According to another aspect of the present invention, an apparatus for providing an in vivo assessment of loads on adjacent bones comprises a body for insertion between the adjacent bones and sensor means for sensing a load being applied to the body through the adjacent bones. The sensor means generates a corresponding output signal in response to and indicative of a sensed load. First circuit means is operatively coupled with the sensor means for receiving the output signal from the sensor means. The first circuit means includes antenna means for receiving energy to power the first circuit means and the sensor means and for transmitting an EMF signal dependent upon the output signal.

In according with another feature of the invention, the apparatus further comprises second circuit means for transmitting energy to power the first circuit means and the sensor means and for receiving the EMF signal. The second means is disposed remote from the first circuit means.

According to yet another aspect of the present invention, an apparatus for providing an in vivo assessment of loads on and motion of one or more bones comprises a member for placement adjacent a bone and at least one sensor associated with the member. The at least one sensor generates an output signal in response to and indicative of a load being applied to the member through the bone. At least one telemetric device is operatively coupled with the at least one sensor. The at least one telemetric device is operable to receive the output signal from the at least one sensor and to transmit an EMF signal dependent upon the output signal.

According to various embodiments of the present invention, the member comprises an implant for helping adjacent bones fuse together, such as a fusion cage, a fixation plate, and/or a bone graft. Alternatively, the member comprises a prosthetic device for preserving motion between adjacent bones.

According to still another aspect of the present invention, an apparatus for providing an in vivo assessment of loads on and motion of one or more bones comprises at least one sensor attached to a bone. The at least one sensor generates an output signal in response to and indicative of a load on the bone. At least one telemetric device is operatively coupled with the at least one sensor. The at least one telemetric device is operable to receive the output signal from the at least one sensor and to transmit an EMF signal dependent upon the output signal.

The present invention also provides a method for in vivo assessing the loads on adjacent bones to be fused together. According to the inventive method, a body for insertion between the adjacent bones is provided. The body is instrumented with at least one sensor for sensing a load on the body and for generating an output signal indicative of a sensed load. At least one telemetric device is operatively coupled with the at least one sensor to receive the output signal and to transmit an EMF signal dependent upon the output signal. The body is implanted between the adjacent bones. The EMF signal from the at least one telemetric device is then monitored.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
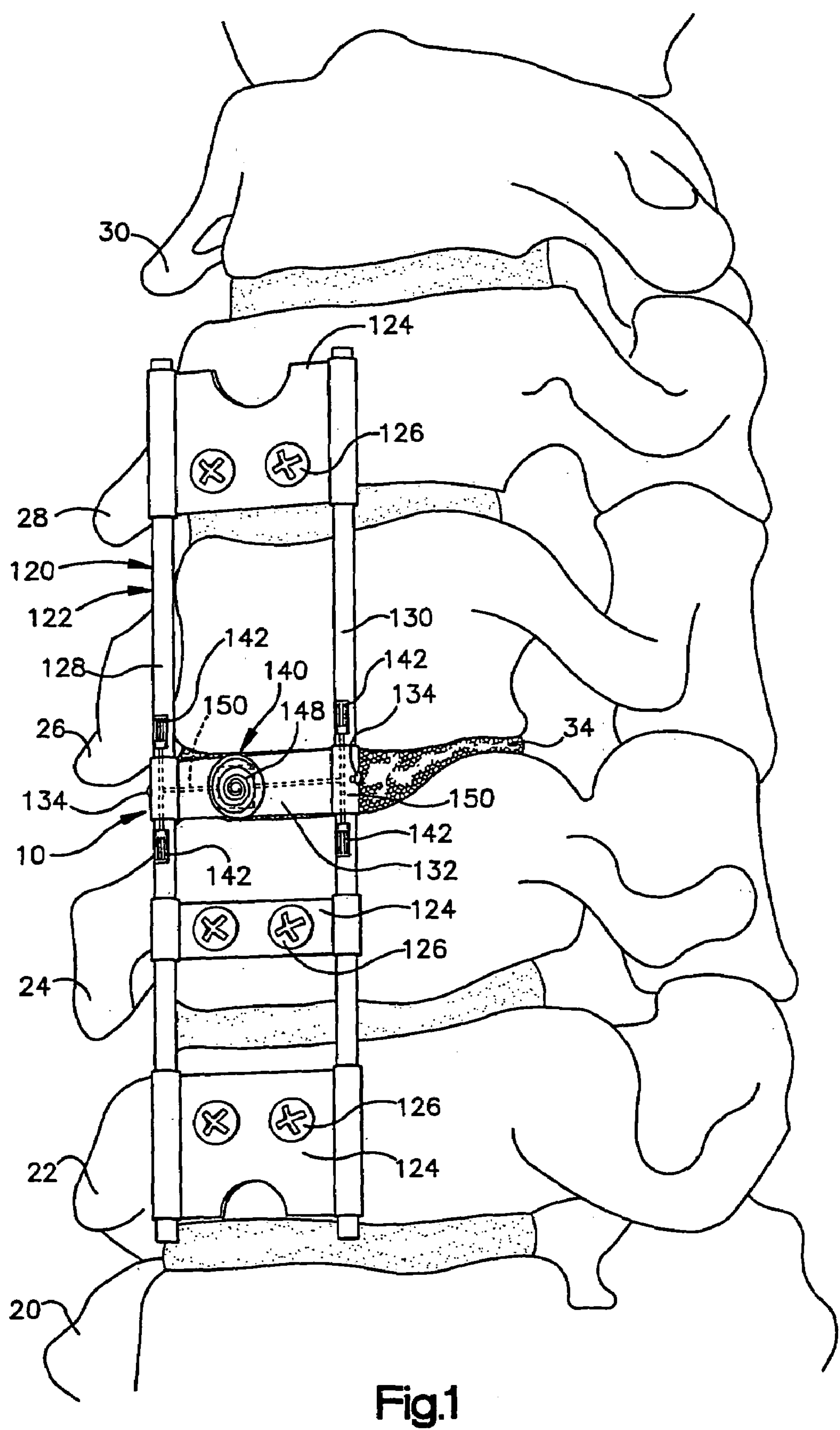
FIG. 1 is a perspective view of a portion of a human spine illustrating an apparatus for providing an in vivo assessment of loads on adjacent bones in accordance with the present invention.

The present invention relates to an apparatus and method for providing an in vivo assessment of loads on adjacent bones. As representative of the present invention, FIG. 1 illustrates several cervical vertebrae in a human spine and an apparatus 10 for providing an in vivo assessment of loads on adjacent cervical vertebrae to be fused together. It should be understood that the apparatus 10 could be used to assess loads and motion in other regions of the human spine. Further, it should also be understood that basic concept of the apparatus 10 could be used to assess loads on and motion of bones in other areas of the human body such as, for example, hip and knee joints, as well as loads on and motion of cartilage, muscles, ligaments, and tendons associated with various bones.

Figure 2:
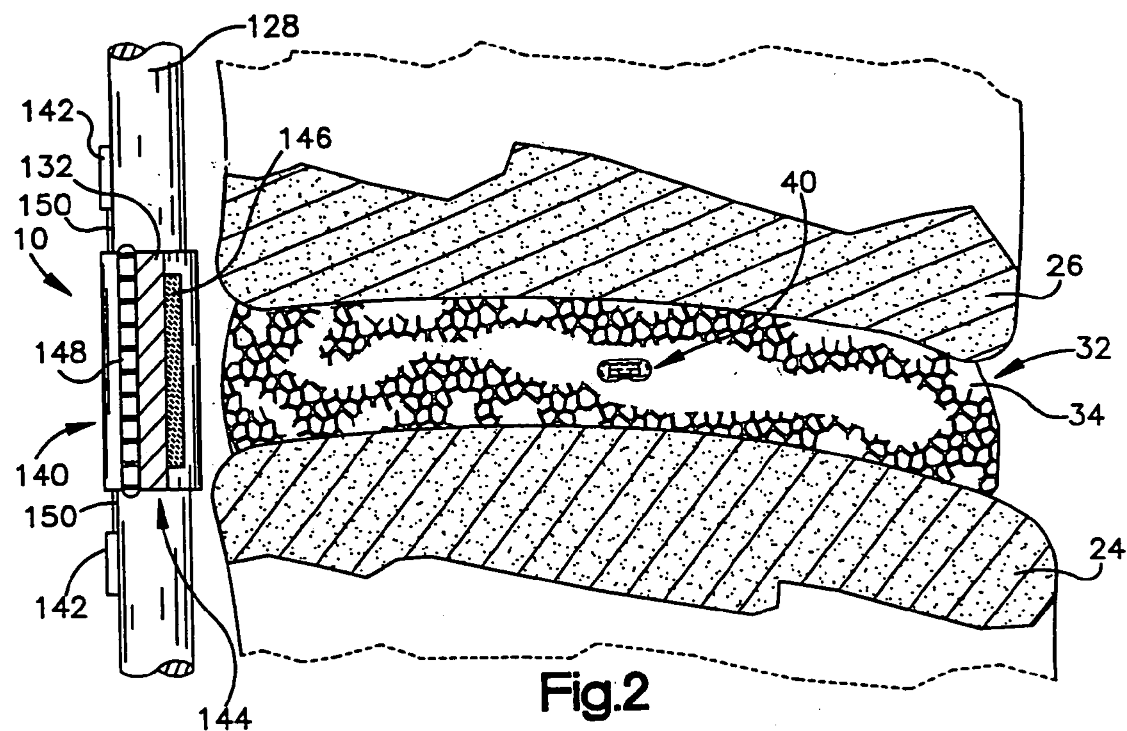
FIG. 2 is a side view, taken in section, illustrating the apparatus of FIG. 1.

Cervical vertebrae C2–C7, identified by reference numbers 20–30, respectively, are shown in FIG. 1. A discectomy has been performed to remove a problematic intervertebral disc (not shown) between two vertebrae (indicated by reference numbers 24 and 26). The removal of the disc leaves an intervertebral space 32 (FIG. 2) between the vertebrae 24 and 26. The intervertebral space 32 is to be filled with a body of bone graft material. In the illustrated embodiment, the body of bone graft material is an autograft 34 harvested from the patient undergoing the discectomy, but the body of bone graft material could alternatively be an allograft, heterograft, or a graft made of a synthetic, biocompatible material.

Prior to insertion of the autograft 34 into the space 34 between the vertebrae 24 and 26, a small passage (not shown) is drilled into the cancellous bone in the interior of the autograft. A transducer assembly 40 placed into the interior of the autograft 34 through a small cannula (not shown). To place the transducer assembly 40 into the autograft 34, the transducer assembly is first loaded into one end of the cannula, and the end of the cannula is then inserted into the passage in the autograft. Morselized cancellous bone may also be placed into the cannula to protect the transducer assembly 40 and to assist in moving the transducer assembly from the end of the cannula into the interior of the autograft 34. Following placement of the transducer assembly 40 inside the autograft 34, the cannula is removed. The passage may then be filled with additional morselized cancellous bone to close and seal the passage.

The transducer assembly 40 comprises a pressure sensor 42 and a telemetric device 44. The transducer assembly 40 is encased in a shell 46 made of a biocompatible metal, such as titanium, or other suitable biocompatible material. As may be seen in FIG. 3, a portion of the shell 46 has a recess 48 defining a thin wall section 50 that is responsive to external pressure. Inside the shell 46, a pair of spacers 52 separate the transducer assembly 40 from the shell.

The illustrated pressure sensor 42 is of a known configuration and is made using known micromachining processes, microfabrication processes, or other suitable MEMS fabrication techniques. Pressure sensors of this type are commercially available from Motorola, Inc. of Schaumburg, Ill. and TRW Novasensor of Fremont, Calif. It should be understood that any pressure sensor that meets the biocompatibility and size requirements (less than two $mm^3$) may be used.

Figure 4:
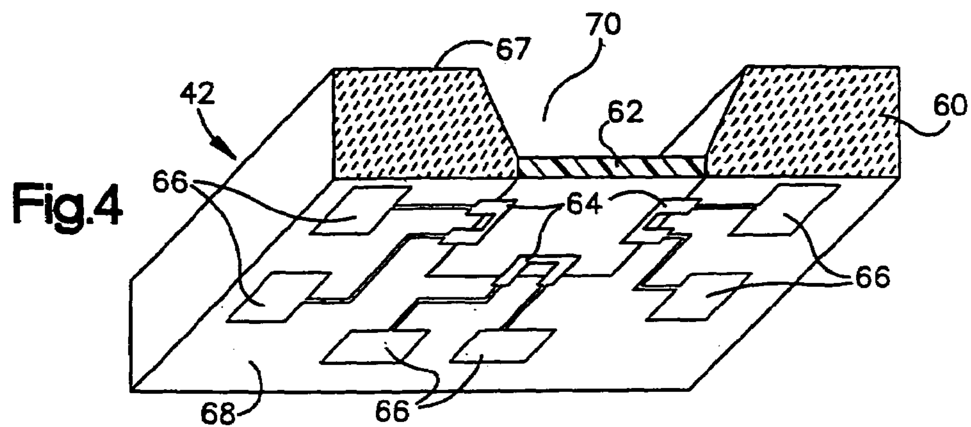
FIG. 4 is a perspective view taken along line 4—4 in FIG. 3.

The illustrated pressure sensor 42 is a piezoresistive device, but it should be understood that other types of pressure sensors, such as a piezoelectric and capacitive sensors, could be substituted. As best seen in FIG. 4, the pressure sensor 42 comprises a substrate 60, a sensing diaphragm 62, a plurality of patterned resistors 64, and a plurality of bond pads 66, two of which are associated with each of the resistors.

The substrate 60 has upper and lower surfaces 67 and 68, respectively, and is made of silicon, but could alternatively be made of another suitable material. The substrate 60 has a well region 70 that extends between the upper and lower surfaces 67 and 68 and that is formed using a conventional microfabrication and bulk micromachining processes including lithography and etching. The sensing diaphragm 62, which extends across the well region 70, is also made of silicon and is defined by the lithography and etching processes. The resistors 64 and the bond pads 66 are formed from a metal layer that is deposited, patterned, and etched in a known manner on the lower surface 68 of the substrate 60. The resistors 64 could also be formed by doping the silicon using boron, phosphorus, arsenic, or another suitable material to make it highly conductive. The resistors 64 are positioned along the edges of the sensing diaphragm 62 to detect strain in the sensing diaphragm caused by pressure differentials.

The telemetric device 44 in the transducer assembly 40 comprise an electronics module 80 (FIG. 3) and an antenna 82. The electronics module 80 is operatively coupled to the pressure sensor 42 by the bond pads 66 in a manner not shown. As shown in the block diagram of FIG. 6, the electronics module 80 comprises an integrated circuit. It is contemplated that an application specific integrated circuit (ASIC) could be designed to incorporate the electronics module 80 and the antenna 82.

The integrated circuit includes an RF-DC converter/modulator 84 and a voltage regulator 86 operatively coupled between the antenna 82 and the pressure sensor 42. The integrated circuit further includes a microprocessor 88 operatively coupled between the pressure sensor 42 and the RF-DC converter/modulator 84. To protect the circuitry of the electronics module 80, the electronics module may be coated with a soft polymeric film, such as parylene or polydimethylsiloxane (PDMS), or a biocompatible epoxy.

Figure 3:
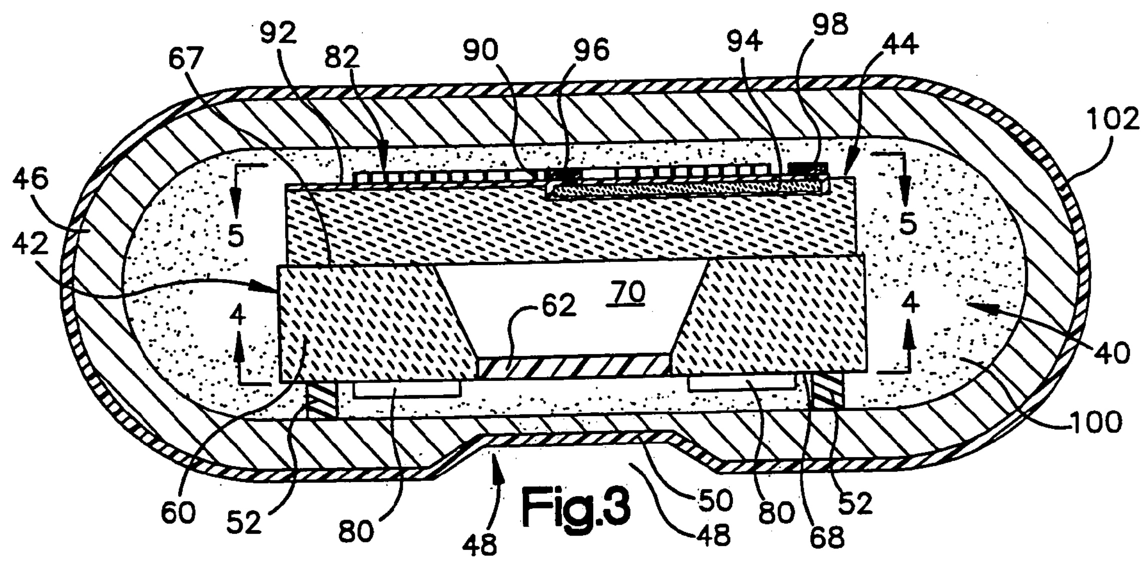
FIG. 3 is a sectional view of a component of the apparatus shown in FIG. 2.
Figure 5:
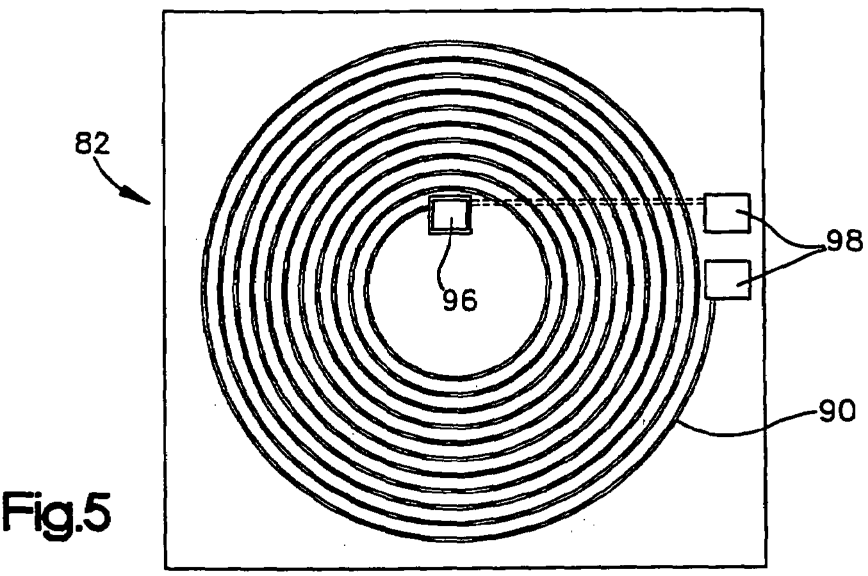
FIG. 5 is a plan view taken along line 5—5 in FIG. 3.

The antenna 82 may be fabricated on the substrate of the pressure sensor 42 using known micromachining or microfabrication techniques, or may alternatively be fabricated separately and joined with the pressure sensor. The antenna 82 comprises a spiral-shaped coil 90 (FIG. 5) of metal deposited over an oxide layer 92 (FIG. 3). A layer of doped polysilicon 94 underneath the oxide layer establishes an electrical connection between a contact 96 in the center of the coil 90 and one of two contacts 98 outside the coil. The contacts 98 of the antenna 82 outside of the coil 90 are operatively coupled with the electronics module 80 in a manner not shown. For protection purposes, the antenna 82 may be coated with a soft polymeric film, such as parylene or PDMS, or a biocompatible epoxy.

Before the shell 46 of the transducer assembly 40 is sealed shut, in a manner not shown, to encapsulate the transducer assembly, the interior of the shell is filled with a silicone gel 100, sol-gel, or other suitable material that is dielectric and biocompatible. The properties of the gel 100 allow it to transmit pressure exerted against the thin section 50 of the shell 46 uniformly against the sensing diaphragm 62 of the pressure sensor 42, while isolating the electrical components and circuitry of the transducer assembly 40 from any corrosive media.

The shell 46 containing the transducer assembly 40 is then packaged within a biomolecular coating 102. Exposing the shell 46 to solutions containing desired biomolecules, such as collagen or hyaluronan, leads to monolayer coating of the outer surface of the shell 46. Alternatively, the outer surfaces of the shell 46 may be coated with thin layers of a soft biocompatible material, such as parylene or PDMS.

Figure 3A:
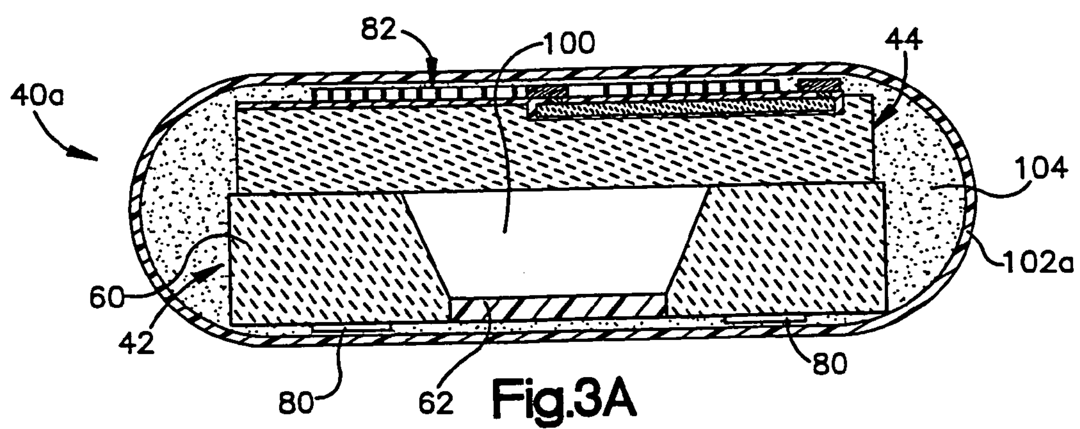
FIG. 3A is a view similar to FIG. 3 illustrating an alternate construction of the component.

FIG. 3A illustrates an alternate configuration for the transducer assembly 40, indicated by the suffix "a". The difference between the transducer assembly 40 of FIG. 3 and the transducer assembly 40*a* of FIG. 3A is that the shell 46 has been omitted. The transducer assembly 40*a* is simply coated with a biocompatible polymeric film 104, such as parylene or PDMS, or a biocompatible epoxy. The transducer assembly may then also packaged within a biomolecular coating 102*a*, as described above.

Returning now to the first embodiment of the present invention, when the transducer assembly 40 is positioned inside the autograft 34 as described above, the autograft is ready to be inserted into the intervertebral space 32 between the vertebrae 24 and 26. Insertion of the autograft 34 into the intervertebral space 32 involves a distraction procedure known in the art.

After the autograft 34 has been inserted between the vertebrae 24 and 26, a spinal fixation implant 120 (FIG. 1) is connected to the cervical vertebrae 22, 24, and 28 to stabilize the vertebrae 20–30 while the autograft 34 fuses the adjacent vertebrae 24 and 26 together. According to the illustrated embodiment, the implant 120 comprises a modified version of the DOC™ Ventral Cervical Stabilization System (hereinafter referred to as the "DOC™ system 122"), available from the DePuy/AcroMed division of Johnson & Johnson, described in U.S. Pat. Nos. 5,843,082 and 6,036,693. It should, however, be understood that the implant 120 could be any type of implanted orthopedic instrumentation or device.

The DOC™ system 122 includes a plurality of plates 124 that are anchored to the vertebrae by screws 126 and interconnected by first and second rods 128 and 130. A platform 132 also extends between the rods 128 and 130 and is secured to the rods by setscrews 134. The platform 132 is positioned over the inserted autograft 34.

A second transducer assembly 140, comprising a plurality of strain gauges 142 and a second telemetric device 144, is mounted to the DOC™ system. The second telemetric device 144 is constructed like the telemetric device described above and comprises a second electronics module 146 and a second antenna 148, both of which are shown only schematically in FIG. 2. The second electronics module 146 is located on a first side of the platform 132 facing toward the autograft 34, while the second antenna 148 is located on an oppositely disposed second side of the platform 132.

Figure 6:
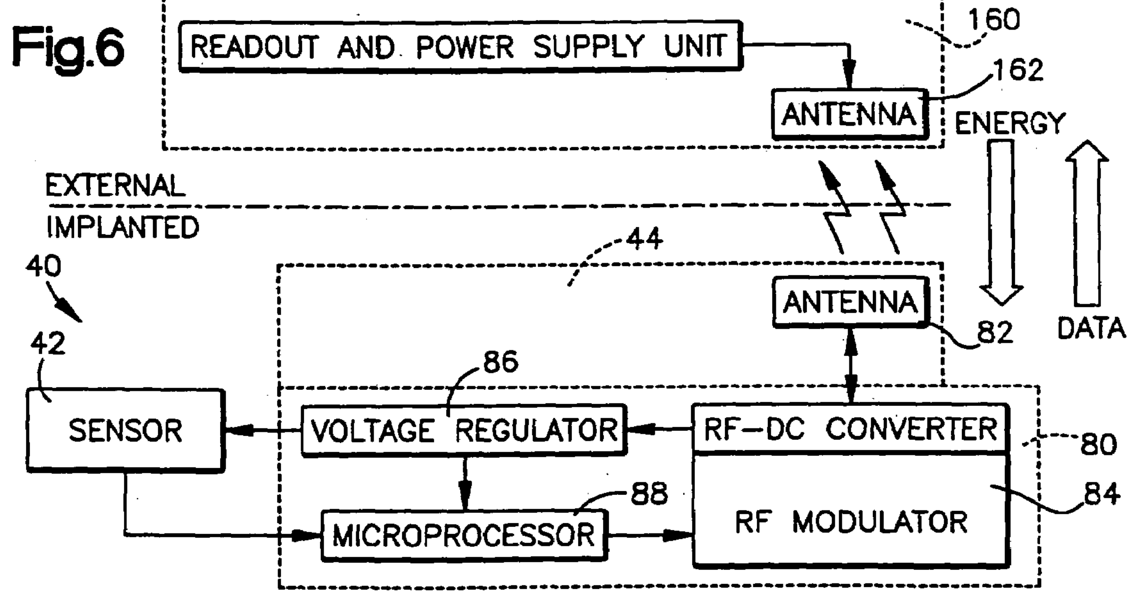
FIG. 6 is a schematic block diagram of the apparatus for providing an in vivo assessment of loads on adjacent bones.

The second electronics module 146 has the basic construction as the electronics module 80 in the transducer assembly 40 illustrated in FIG. 6. The second electronics module 146 comprises an integrated circuit that is operatively coupled to the second antenna 148 on the second side of the platform 132 in manner not shown. To protect its circuitry, the second electronics module 146 may be coated with a soft polymeric film, such as parylene or PDMS, or a biocompatible epoxy.

As may be seen in FIG. 1, the second antenna 148 is larger in overall size than the antenna 82 in the transducer assembly 40, but has the same basic configuration and construction. The second antenna 148 may be fabricated using known MEMS fabrication or micromachining techniques, or any other conventional microelectronic fabrication process. The second antenna 148 comprises a spiral-shaped coil of metal deposited over an oxide layer. A layer of doped polysilicon underneath the oxide player establishes an electrical connection between a contact in the center of the coil and a contact outside the coil. For protection purposes, the antenna 82 may be coated with a soft polymeric film, such as parylene or PDMS, or a biocompatible epoxy.

In accordance with the apparatus 10, the first and second rods 128 and 130 of the DOC™ system 122 are instrumented with the plurality of strain gauges 142. The strain gauges 142 may be commercially available devices, such as those produced by microelectronics suppliers such as Vishay Inc. and MicroMeasurements Inc., or may be custom-fabricated by a foundry. Two of the strain gauges 142 are secured to the first rod 128 above and below, respectively, the platform 132. The strain gauges 142 are operatively coupled to the second electronics module 146 by electrical leads in the form of metal traces 150 deposited on the surface of an insulating film (not shown) covering the first rod 128 and the side of the platform 132. Alternatively, the electrical ends could be insulated wires threaded through the inside of the rod 128 to make contact. For protection purposes, the strain gauges 142 and the electrical traces 150 may be coated with a soft polymeric film, such as parylene or PDMS, a biocompatible epoxy, or a monolayer of biomolecular coating.

Similarly, another two strain gauges 142 are secured to the second rod 130 above and below, respectively, the platform 132. These two strain gauges 142 are also operatively coupled to the second electronics module 146 by electrical leads in the form of metal traces 150 deposited on the surface of the second rod 130 and the side of the platform 132. Again, the strain gauges 142 and the electrical traces 150 associated with the second rod 130 may be coated with a soft polymeric film, such as parylene or PDMS, or a biocompatible epoxy.

The apparatus 10 further includes an external (meaning it is located outside of and/or remote from the patient's body) readout/power supply unit 160 (FIG. 6) having an integrated antenna 162. The readout/power supply unit 160 contains circuitry known in the art and therefore not described in any detail. The readout/power supply unit 160 may be a handheld device or a larger piece of equipment found at a physician's office. The readout/power supply unit 160 could also be a device worn by the patient.

The readout/power supply unit 160 is operable to transmit electrical energy and receive data through the antenna 162 as described further below. Further, the readout/power supply unit 160 is able to display and store the received data.

Following implantation of the instrumented autograft 34 and the instrumented DOC™ system 122 into the spine as described above, the apparatus 10 can be used to provide an in vivo assessment of the bony incorporation of the autograft, and thus the fusion of the autograft and the vertebrae 24 and 26, as well as the biomechanical performance of the DOC™ system. The readout/power supply unit 160 transmits electrical energy in the form of an electromagnetic field (EMF) signal, or more specifically a radio frequency (RF) signal, through the antenna 162 to the transducer assembly 40 in the autograft 34 and to the transducer assembly 140 on the platform 132. The RF signal is received through the antennas 82 and 148 in each of the transducer assemblies 40 and 140, respectively, and is converted into a DC signal to energize the circuitry in the sensor assemblies, including the pressure sensor 42 and the strain gauges 142.

The pressure sensor 42 in the autograft 34 detects changes in electrical resistance caused by deformation and strain on the sensing diaphragm 62. The changes in resistance detected by the pressure sensor 42 correspond to applied pressure and a data signal dependent upon the sensed condition is generated by the electronics module 80. The data signal is then transmitted percutaneously from the antenna 82 to the antenna 162 in the readout/power supply unit 160. The data signal transmitted is a pulse-width-modulated (PWM) signal that has an RF carrier frequency. It should be understood that other signal types (e.g., frequency modulation (FM) or frequency shift key (FSK)) could also be used.

The antenna 162 in the readout/power supply unit 160 receives the data signal from the transducer assembly 40, processes the data signal, and displays pressure data based on the data signal that correspond to the pressure sensed by the pressure sensor 42. The pressure data may be displayed in any number of formats, such as absolute values or plots. The pressure data may also be stored by the readout/power supply unit 160.

While the readout/power supply unit 160 is providing electrical power to and receiving data from the transducer assembly 40 in the autograft 34, the readout/power supply unit 160 is also doing the same with the second transducer assembly 140 on the DOC™ system 122. The implanted strain gauges 142 detect changes in strain on the rods 128 and 130. The electronics module 146 on the platform 132 generates data signals dependent upon the sensed changes in strain. These data signals are then transmitted percutaneously from the antenna 148 to the antenna 162 in the readout/power supply unit 160. As above, the data signals transmitted are a pulse-width-modulated (PWM) signals that have an RF carrier frequency, but could be other signal types (e.g., frequency modulation (FM) or frequency shift key (FSK)).

The antenna 162 in the readout/power supply unit 160 receives the data signals from the second transducer assembly 140, processes the data signals, and displays strain data based on the data signals that correspond to the strain on the rods 128 and 130. The strain data may be displayed in any number of formats, and may also be stored by the readout/power supply unit 160.

The pressure data and the strain data received by the readout/power supply unit 160 provide an in vivo assessment of the bony incorporation of the autograft 34, and thus the fusion of the autograft and the vertebrae 24 and 26, as well as the biomechanical performance of the DOC™ system 122. For example, an expected pattern of loads detected by the pressure sensor 42 will initially involve pressure oscillations that dampen over time, with an overall increase in applied pressure indicative of bone incorporation of the autograft 34. On the other hand, an expected pattern of strain detected by the strain gauges 142 will initially involve large axial forces that will decrease over time as the DOC™ system 122 shares more of the load with the vertebrae 24 and 26 that are being fused by the autograft 34. If the data from the pressure sensor 42 and the strain gauges 142 follows or deviates from the expected patterns, conclusions can be drawn about progress of the fusion between the autograft 34 and the vertebrae 24 and 26, as well as the biomechanical performance of the DOC™ system 122.

The apparatus 10 described above provides the ability to continuously, or on-demand, monitor fusion progress and biomechanical performance during the post-operative period by assessing the loads on the autograft 34 and on the spinal fixation instrumentation. Because of this ability to continuously or on-demand monitor fusion progress and biomechanical performance, it may be possible to appropriately time, or even avoid, additional surgery. Further, information gathered from such in vivo assessments can lead to improvements in surgical techniques and spinal implant design.

Figure 7:
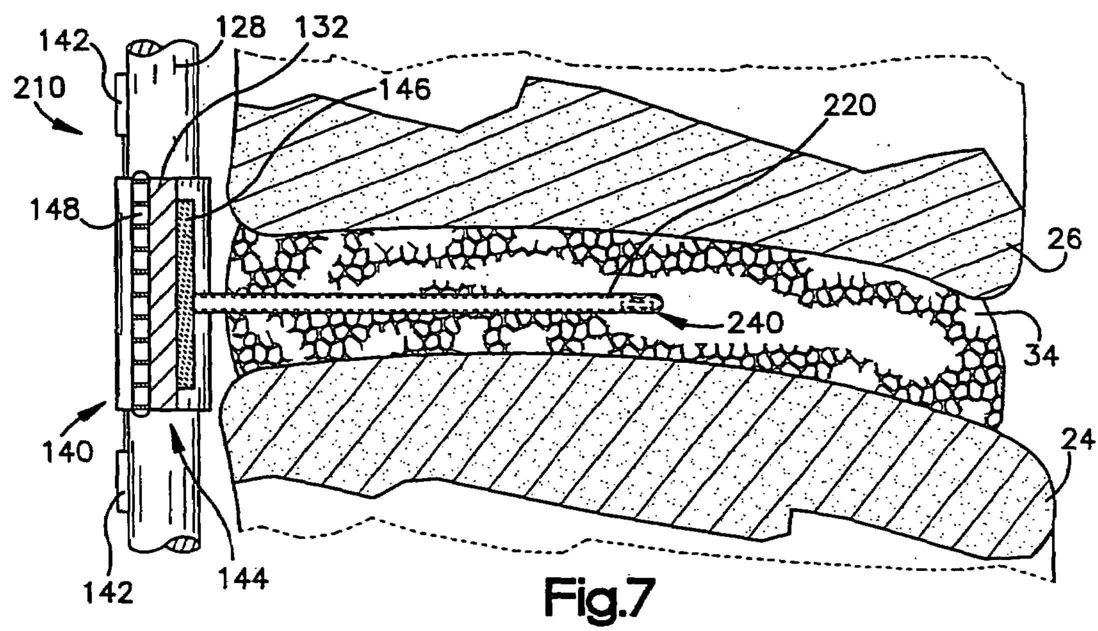
FIG. 7 is a side view, similar to FIG. 2, illustrating an apparatus for providing an in vivo assessment of loads on adjacent bones constructed in accordance with a second embodiment of the present invention.
Figure 8:
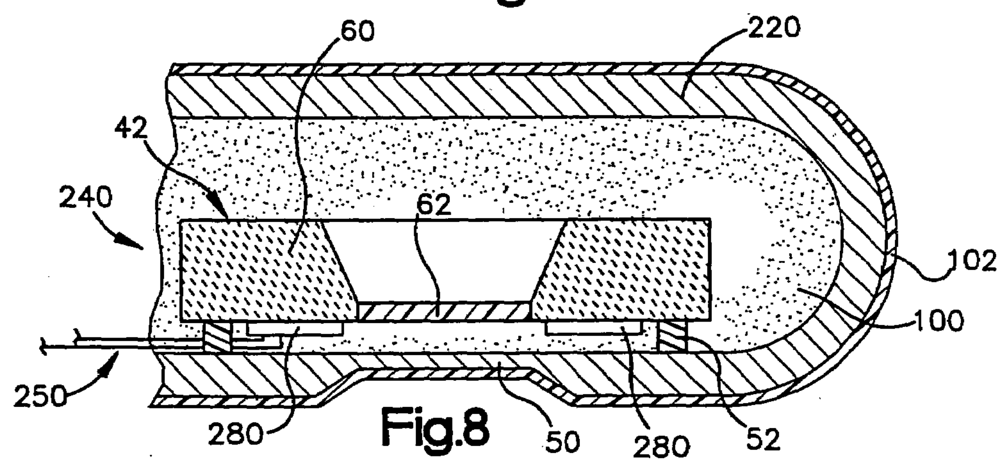
FIG. 8 is a sectional view, similar to FIG. 3, showing a component of the apparatus of FIG. 7.

FIGS. 7 and 8 illustrate an apparatus 210 for providing an in vivo assessment of loads on adjacent bones constructed in accordance with a second embodiment of the present invention. In the second embodiment of FIGS. 7 and 8, reference numbers that are the same as those used in the first embodiment of FIGS. 1–6 designate components that are the same as components in the first embodiment.

According to the second embodiment, a tube 220 replaces the shell 46 and encapsulates a transducer assembly 240. The tube 220 is made of metal, such as titanium, and is fixedly attached to the platform 132 of the DOC™ system in a manner not shown. The transducer assembly 240 is positioned inside the end of the tube 220 and coated inside the tube with a dielectric gel as described above. The tube 220 is inserted into the passage drilled into the autograft 34 so that the transducer assembly 240 is located approximately in the middle of the autograft.

The tube 220 containing the transducer assembly 240 may be packaged within a biomolecular coating. Exposing the tube 220 to solutions containing desired biomolecules, such as collagen or hyaluronan, leads to monolayer coating of the outer surface of the tube. Alternatively, the outer surfaces of the tube 220 may be coated with thin layers of a soft biocompatible material, such as parylene or PDMS.

The transducer assembly 240 comprises the pressure sensor 42 described above, but could alternatively utilize another suitable type of micromachined/microfabricated sensor. Unlike the transducer assembly 40 described above, the transducer assembly 240 does not include an antenna. Rather, wires 250 (FIG. 8) extend through the tube 220 to electrically connect the electronics module 146 on the platform 132 to an electronics module 280 in the transducer assembly 240. The wires 250 carry electrical power from the second transducer assembly 140 to the transducer assembly 240 in the autograft 34. The wires 250 also carry data signals from the pressure sensor 42 back to the second transducer assembly 140 for transmission over the antenna 148 on the platform 132.

The apparatus 210 according to the second embodiment functions in the same manner as the apparatus of the first embodiment to provide a continuous or on-demand in vivo assessment of the bony incorporation of the autograft 34, and thus the fusion of the autograft and the vertebrae 24 and 26, as well as the biomechanical performance of the DOC™ system.

Figure 9:
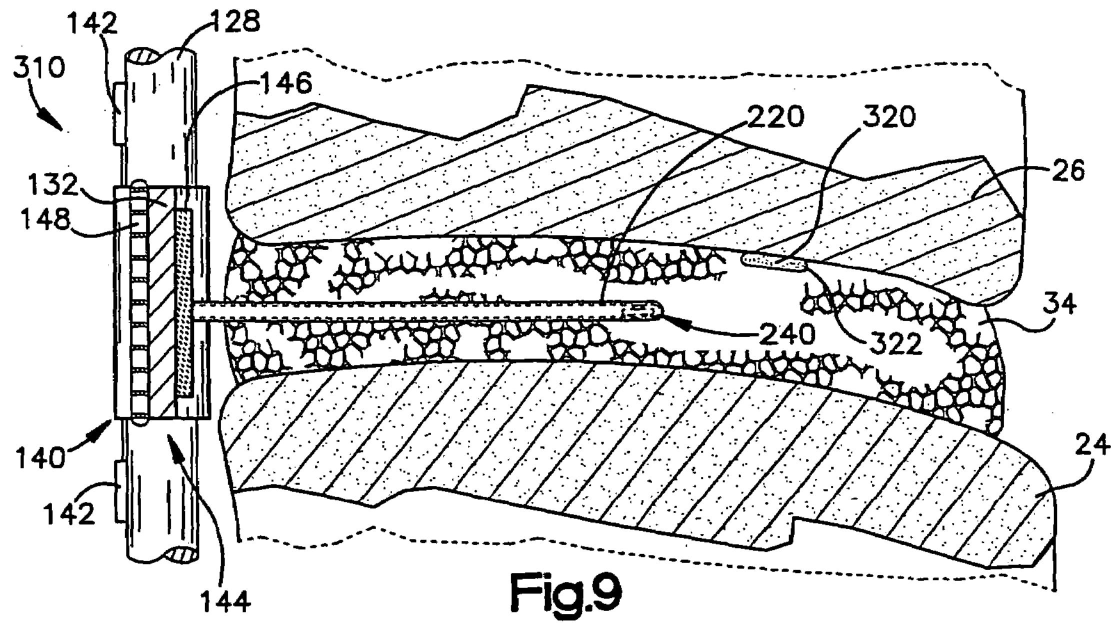
FIG. 9 is a side view, similar to FIG. 2, illustrating an apparatus for providing an in vivo assessment of loads on adjacent bones constructed in accordance with a third embodiment of the present invention.

FIG. 9 illustrates an apparatus 310 for providing an in vivo assessment of loads on adjacent bones constructed in accordance with a third embodiment of the present invention. In the third embodiment of FIG. 9, reference numbers that are the same as those used in FIGS. 1–8 designate components that are the same as components shown in FIGS. 1–8.

According to the third embodiment, the apparatus 310 includes a load cell 320. The load cell 320 is countersunk into the upper surface (as viewed in the Figures) of the autograft 34 facing the vertebrae 26. It should be understood, however, that the load cell 320 could be positioned in any number of locations in the autograft 34. Further, it is contemplated that more than one load cell 320 could be positioned in the autograft 34.

Like the transducer assembly 40 illustrated in FIG. 3, the load cell 320 includes a sensing element (not shown) and an integral telemetry device (not shown) constructed using MEMS and/or microelectronic fabrication techniques. The telemetry device includes an electronics package and an antenna. The sensing element in the load cell 320 may be a piezoresistive device, a piezoelectric device, a capacitive device, a strain gauge-based device, or any other suitable device. Using an RF carrier signal, the load cell 320 is inductively powered and interrogated for data in the same manner as the transducer assembly 40 described in the first embodiment.

The load cell 320 has an outer housing 322 that may be packaged within a biomolecular coating. Exposing the outer housing 322 of the load cell 320 to solutions containing desired biomolecules, such as collagen or hyaluronan, leads to monolayer coating of the surface of the outer housing 322. Alternatively, the outer housing 322 of the load cell 320 may be coated with thin layers of a soft biocompatible material, such as parylene or PDMS.

The apparatus 310 according to the third embodiment functions in a similar manner to the apparatus 10 of the first embodiment to provide a continuous or on-demand in vivo assessment of the bony incorporation of the autograft 34, and thus the fusion of the autograft and the vertebrae 24 and 26, as well as the biomechanical performance of the DOC™ system 122. The addition of the load cell 320 in the apparatus provides additional data for the physician to assess the bone in-growth and biomechanical performance of the implant.

Figure 10:
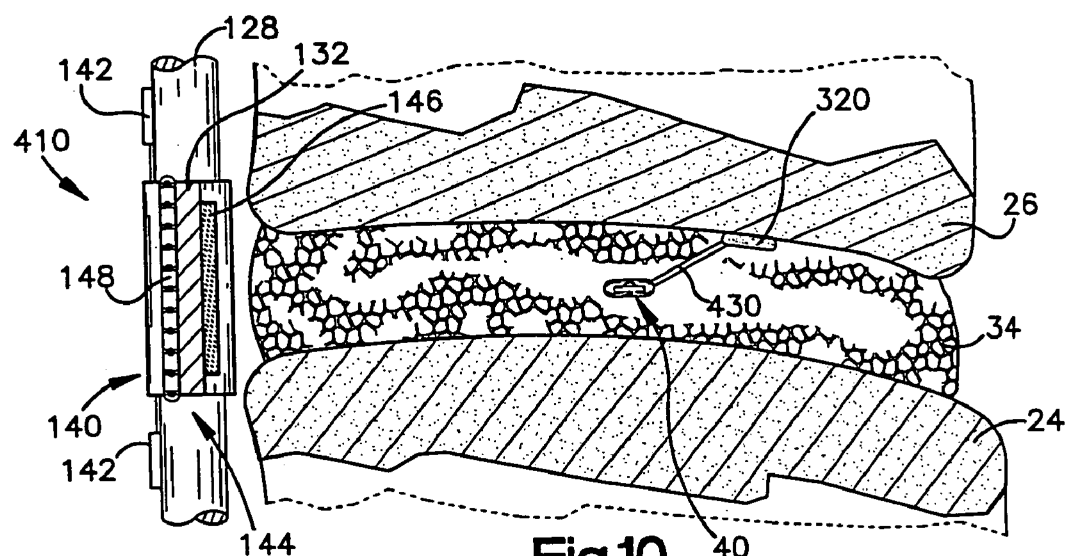
FIG. 10 is a side view, similar to FIG. 2, illustrating an apparatus for providing an in vivo assessment of loads on adjacent bones constructed in accordance with a fourth embodiment of the present invention.

FIG. 10 illustrates an apparatus 410 for providing an in vivo assessment of loads on adjacent bones constructed in accordance with a fourth embodiment of the present invention. In the fourth embodiment of FIG. 10, reference numbers that are the same as those used in FIGS. 1–9 designate components that are the same as components shown in FIGS. 1–9.

According to the fourth embodiment, the apparatus 410 includes the first and second transducer assemblies 40 and 140, as well as the load cell 320. A tube 430 extends between the transducer assembly 40 in the autograft 34 and the load cell 320 in the upper surface of the autograft. As above, it should be understood that the load cell 320 could be positioned in any number of locations in the autograft 34.

Unlike the load cell 320 described above in the third embodiment, the load cell 320 does not include an antenna. Rather, wires (not shown) extend through the tube 430 to electrically connect any electronics module (not shown) in the load cell 320 to the electronics module 80 in the transducer assembly 40. The wires carry electrical power from the transducer assembly 40 to the load cell 320. The wires also carry data signals from the load cell 320 back to the transducer assembly 40 for RF transmission to the readout/power supply device 160.

It should be apparent that a variant of the fourth embodiment would be that a telemetry device, including an electronics module and an antenna, be located in the load cell 320 rather than in the transducer assembly 40. Further, it should also be apparent that another variant of the fourth embodiment would be to use the transducer assembly 240 of FIG. 9, which does not include an electronics module nor an antenna, and the tube 220 that houses wires for exchanging signals.

The apparatus 410 according to the fourth embodiment functions in the same manner as the apparatus 310 of the third embodiment to provide a continuous or on-demand in vivo assessment of the bony incorporation of the autograft 34, and thus the fusion of the autograft and the vertebrae 24 and 26, as well as the biomechanical performance of the DOC™ system 122.

Figure 11:
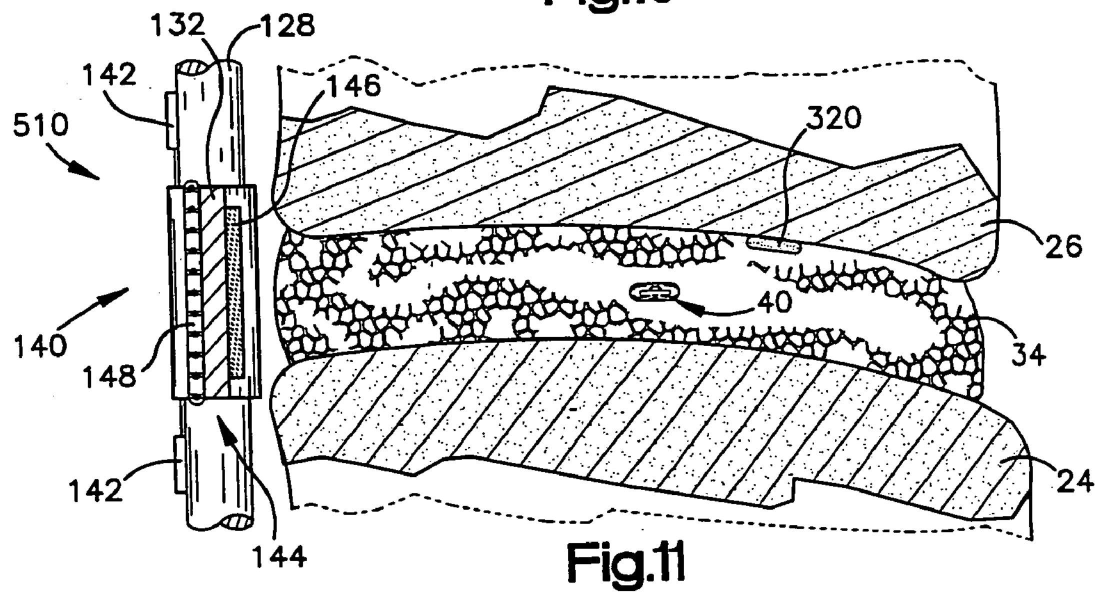
FIG. 11 is a side view, similar to FIG. 2, illustrating an apparatus for providing an in vivo assessment of loads on adjacent bones constructed in accordance with a fifth embodiment of the present invention.

In FIG. 11, an apparatus 510 constructed in accordance with a fifth embodiment of the present invention is illustrated. The fifth embodiment of FIG. 11 is nearly identical to the fourth embodiment of FIG. 10, except that both the transducer assembly 40 and the load cell 320 have integral telemetry devices. As such, the readout/power supply unit 160 thus separately inductively powers and collects data from the load cell 320, the transducer assembly 40 in the autograft 34, and the transducer assembly 140 on the DOC™ system 122. Accordingly, the apparatus 510 functions in the same basic manner as the apparatus 310 of the third embodiment 310 to provide a continuous or on-demand in vivo assessment of the bony incorporation of the autograft 34, and thus the fusion of the autograft and the vertebrae 24 and 26, as well as the biomechanical performance of the DOC™ system 122.

Figure 12:
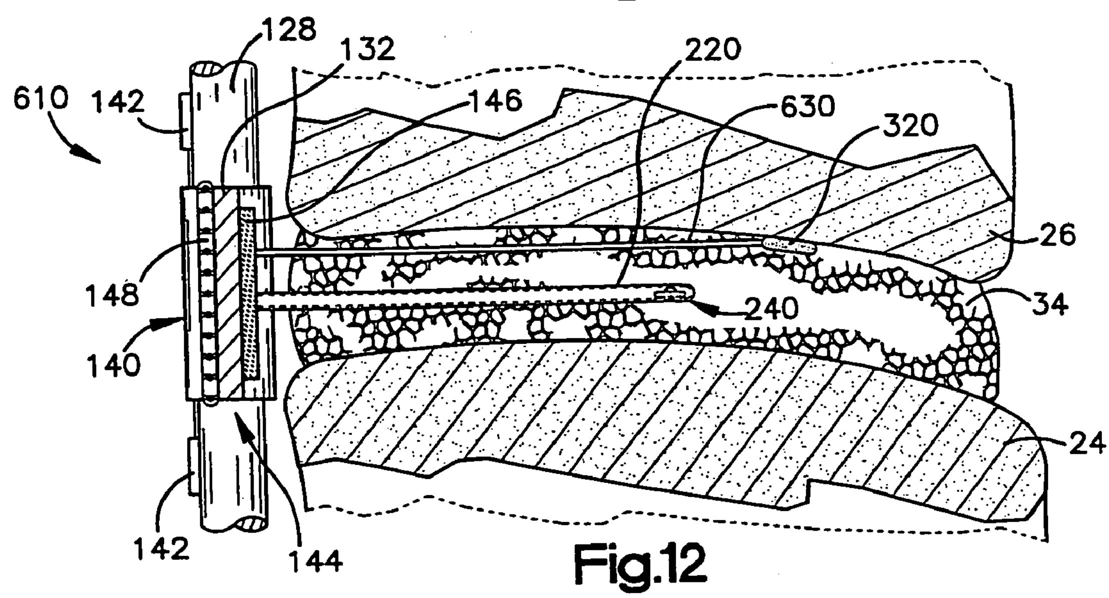
FIG. 12 is a side view, similar to FIG. 2, illustrating an apparatus for providing an in vivo assessment of loads on adjacent bones constructed in accordance with a sixth embodiment of the present invention.

FIG. 12 illustrates an apparatus 610 constructed in accordance with a sixth embodiment of the present invention. The sixth embodiment of FIG. 12 is similar to the third embodiment of FIG. 9, except that in FIG. 12 a second tube 630 connects the load cell 320 to the transducer assembly 140 on the platform 132. This is because the load cell 320 does not have an integral telemetry device and thus wires (not shown) are run through the second tube 630 to carry electrical power and data to and from, respectively, the load cell 320. As such, all of the data from the load cell 320, the pressure sensor 42, and the strain gauges 142 is transmitted over the antenna 148 on the platform 132. Other than this difference, the apparatus 610 according to the sixth embodiment functions in the same basic manner as the apparatus 310 of the third embodiment to provide a continuous or on-demand in vivo assessment of the bony incorporation of the autograft 34, and thus the fusion of the autograft and the vertebrae 24 and 26, as well as the biomechanical performance of the DOC™ system 122.

Figure 13:
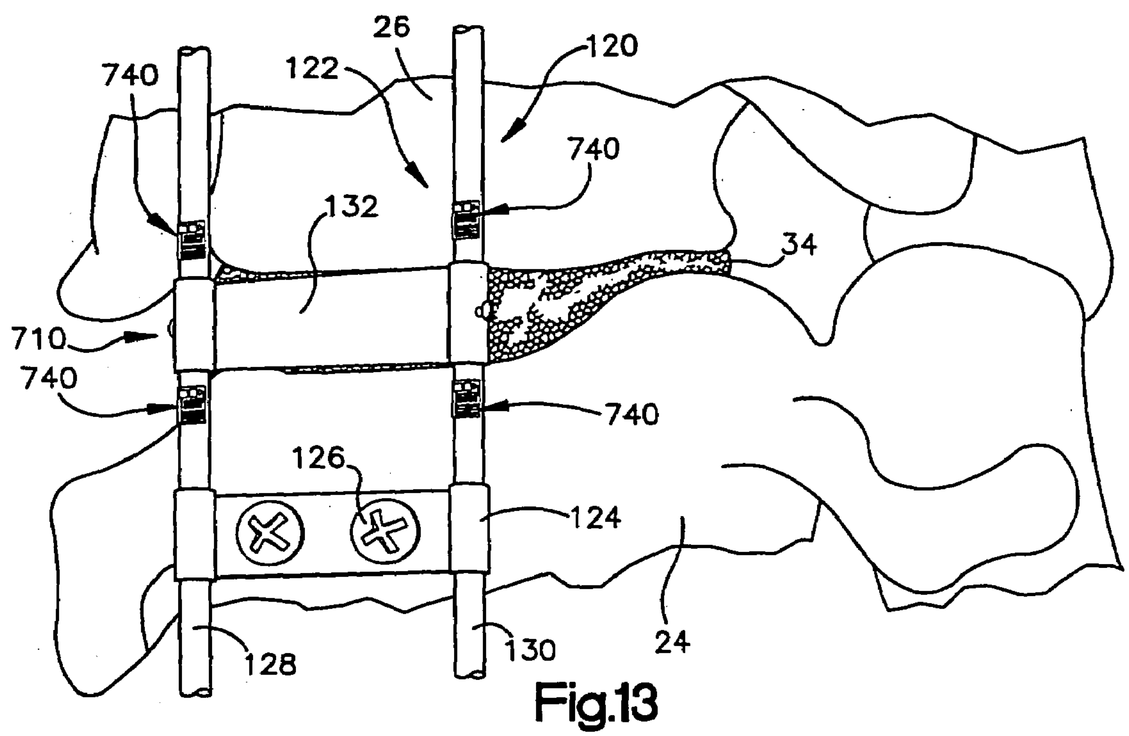
FIG. 13 is a perspective view, similar to FIG. 1, of a portion of a human spine illustrating an apparatus for providing an in vivo assessment of loads on adjacent bones in accordance with a seventh embodiment of the present invention.
Figure 14:
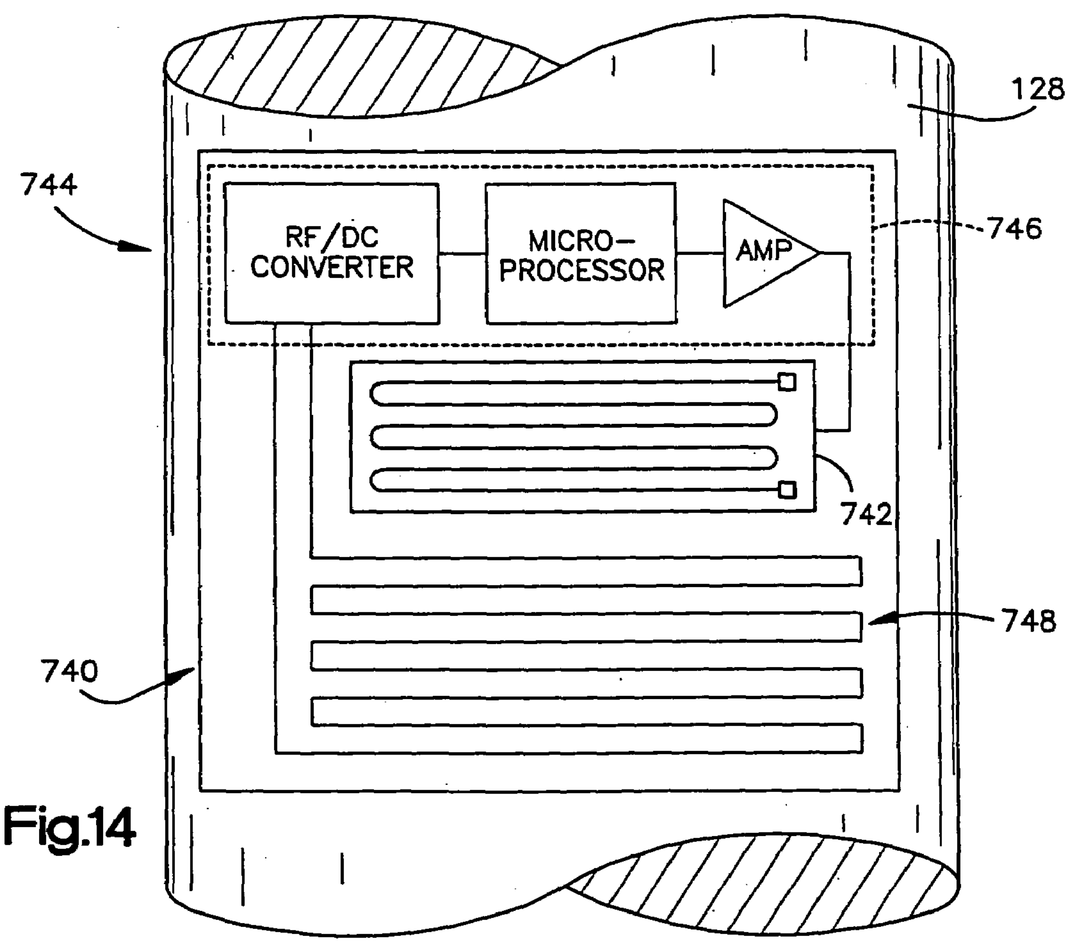
FIG. 14 is an enlarged view illustrating a component of the apparatus of FIG. 13.

FIGS. 13 and 14 illustrate an apparatus 710 for providing an in vivo assessment of loads on adjacent bones constructed in accordance with a seventh embodiment of the present invention. In the seventh embodiment of FIGS. 13 and 14, reference numbers that are the same as those used above designate components that are the same as components described above.

According to the seventh embodiment, the apparatus 710 comprises a plurality of transducer assemblies 740 mounted to the rods 128 and 130 of the DOC™ system 122. Additional transducer assemblies may be located in the autograft 34 as described above, but are omitted from FIGS. 13 and 14 for clarity. Each transducer assembly 740 includes a sensor, such as a strain gauge 742, and an integral telemetry device 744 constructed using MEMS and/or microelectronic fabrication techniques. As best seen in the schematic diagram of FIG. 14, each telemetry device 744 includes an electronics package 746 and an antenna 748. Hence, there are no electronics present on the platform 132. Using RF carrier signals, each strain gauge 742 is inductively powered and interrogated for data in the same manner as the transducer assembly 40 described in the first embodiment.

The apparatus 710 according to the seventh embodiment functions to provide a continuous or on-demand in vivo assessment of the bony incorporation of the autograft 34, and thus the fusion of the autograft and the vertebrae 24 and 26, as well as the biomechanical performance of the DOC™ system 122.

Figure 15:
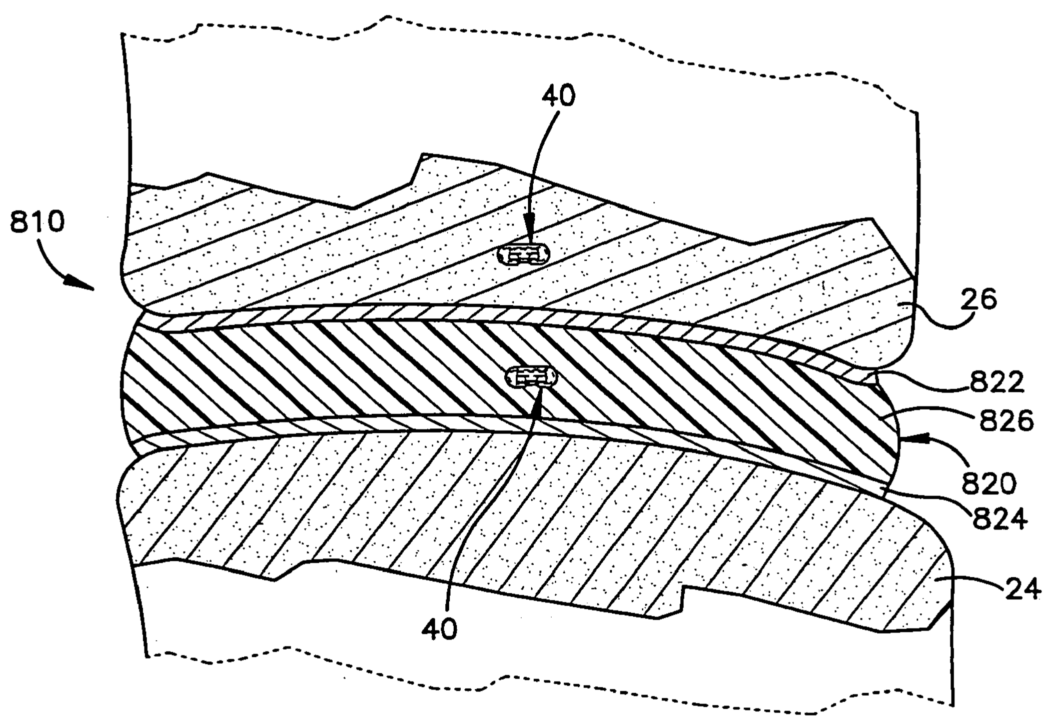
FIG. 15 is a side view, similar to FIG. 2, illustrating an apparatus for providing an in vivo assessment of loads on adjacent bones constructed in accordance with an eighth embodiment of the present invention.

FIG. 15 illustrates an apparatus 810 for providing an in vivo assessment of loads on and motion of a bone in accordance with an eighth embodiment of the present invention. In the eighth embodiment of FIG. 15, reference numbers that are the same as those used above designate components that are the same as components described above.

In accordance with the eighth embodiment, an artificial disc 820 is inserted between the vertebrae 24 and 26 in place of a problematic disc. The artificial disc 820 is intended to carry the loads on the vertebrae 24 and 26 and also preserve the motion of the vertebrae. The artificial disc 820 illustrated in FIG. 15 has upper and lower plates 822 and 824 spaced apart by a flexible polymeric core 826. It should, however, be understood that other configurations of artificial discs could also be used.

Prior to insertion of the artificial disc 820 between the vertebrae 24 and 26, a transducer assembly such as the transducer assembly 40 described in the first embodiment, is positioned within the artificial disc. Additional transducer assemblies (not shown) may also be located in the artificial disc 820. Further, as shown in FIG. 15, it is contemplated that a transducer assembly 40 can be positioned in the interior of a vertebrae, such as the vertebrae 26, by inserting the transducer assembly into a passage drilled in the vertebrae. The apparatus 810 according to the eighth embodiment functions to provide a continuous or on-demand in vivo assessment of the loads on the vertebrae 26 and on the artificial disc 820, as well as provide an assessment of the motion of the artificial disc relative to the vertebrae 24 and 26.

It should be understood that the apparatus 810 could be used in any number of different applications in the human body where it is desirable to assess the loads on one or more bones or on an orthopedic implant. Furthermore, it should also be understood that the apparatus 810 could be used to assess motion of, or between, adjacent bones and/or orthopedic implants. Such additional applications of the apparatus 810 would include most joints in the human body.

Figure 16:
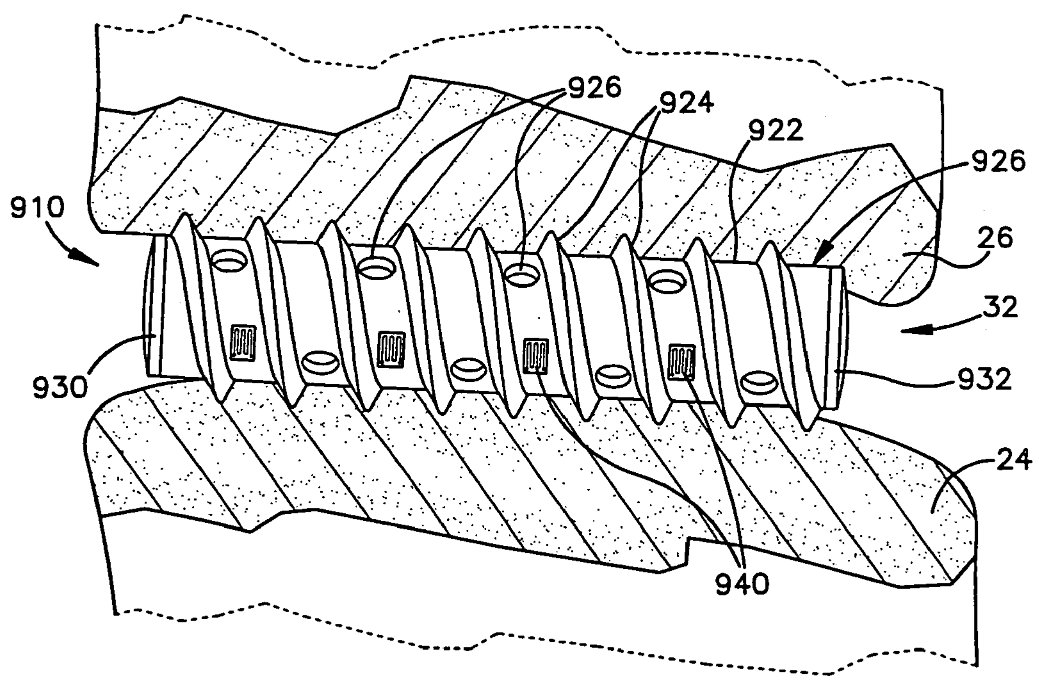
FIG. 16 is a side view, similar to FIG. 2, illustrating an apparatus for providing an in vivo assessment of loads on adjacent bones constructed in accordance with a ninth embodiment of the present invention.
Figure 17:
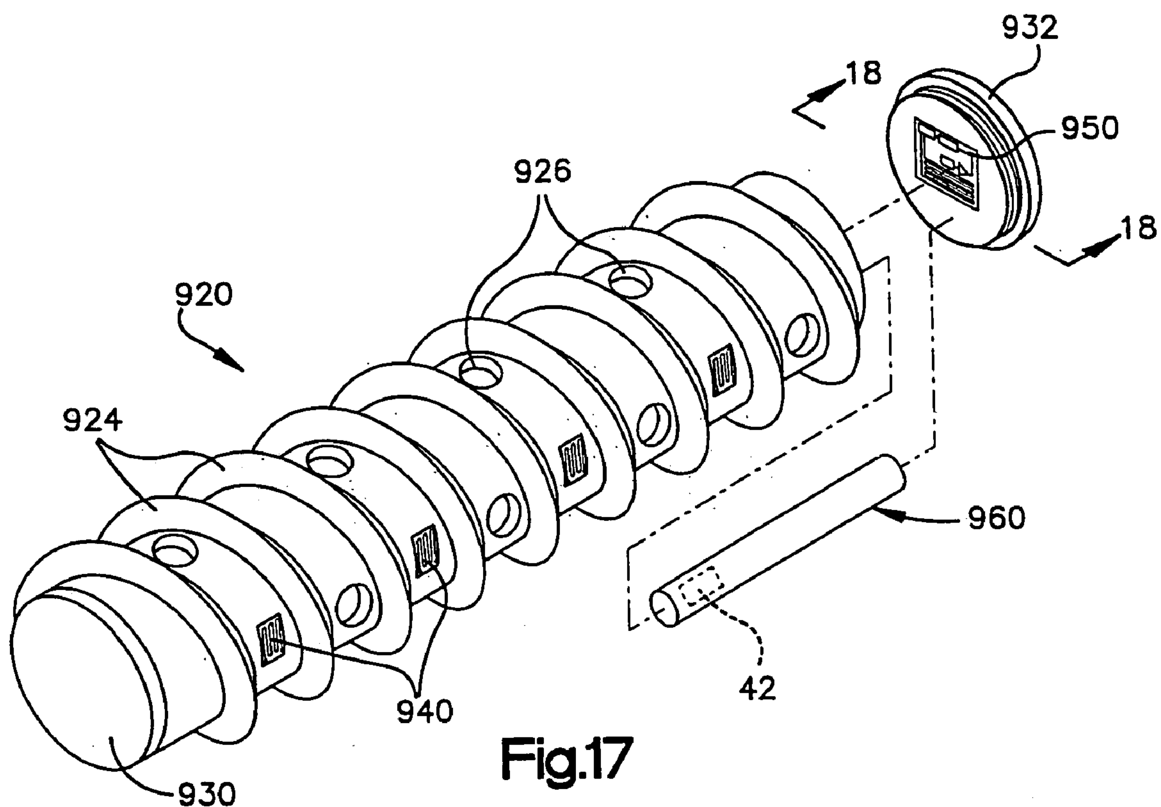
FIG. 17 is a perspective view of a component of the apparatus of FIG. 16.
Figure 18:
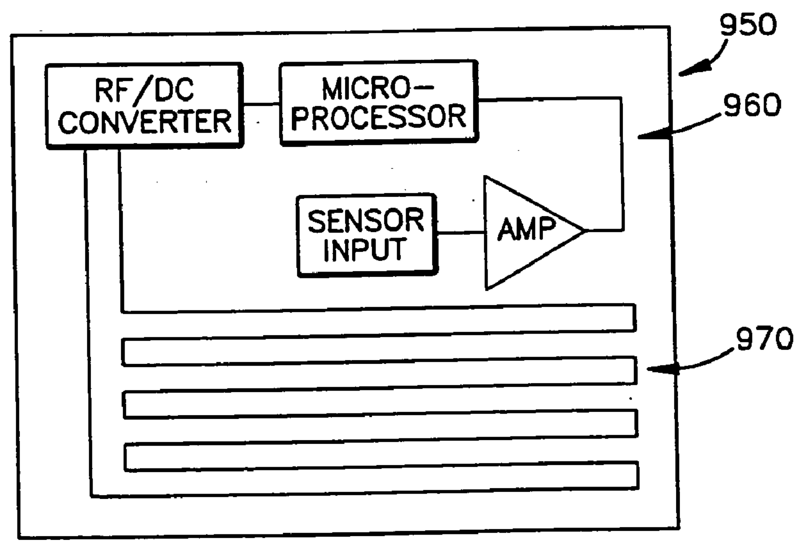
FIG. 18 is a schematic block diagram of another component of the apparatus of FIG. 16.

FIGS. 16–18 illustrate an apparatus 910 for providing an in vivo assessment of loads on adjacent bones constructed in accordance with a ninth embodiment of the present invention. In the ninth embodiment of FIGS. 16–18, reference numbers that are the same as those used above designate components that are the same as components described above.

According to the ninth embodiment, another different type of implant is inserted into the intervertebral space 32 following a discectomy. The implant is an interbody fusion cage 920 known in the art. The fusion cage 920 has a cylindrical outer surface 922 with external threads 924. The fusion cage 920 is screwed into place in the intervertebral space 32 so that the threads 924 bite into the surfaces (also known as endplates) of the vertebrae 24 and 26. As in known in the art, the fusion cage 920 has a plurality of openings 926 that extend through the outer surface 922 and into an interior chamber (not numbered). After the fusion cage 920 is implanted in the vertebrae 24 and 26, the interior chamber is filled with bone graft material, such as bone chips or a synthetic material to promote bone growth. Removable end caps 930 and 932 close the interior chamber after the bone graft material has been placed inside the fusion cage 920. Over time, bone in-growth occurs and the fusion cage 920 fuses the vertebrae 24 and 26 together. The openings 926 in the fusion cage 920 help to facilitate the bone in-growth, and thus, the fusion process.

Prior to implantation of the fusion cage 920, a plurality of strain gauges 940 are installed on the fusion cage. The strain gauges 940 are located in the groove that lies between the threads 924 on the outer surface 922 of the fusion cage 920. The strain gauges 940 may be commercially available devices or custom-fabricated by a foundry. The strain gauges 940 are operatively coupled to a telemetry device 950 located on the end cap 932 by electrical leads in the form of metal traces (not shown) deposited on an insulating film (not shown) or the inside surface of the fusion cage. The traces make electrical contact with traces (not shown) on the end cap 932 when the end cap is attached to the fusion cage 920. Alternatively, the electrical leads could be insulated wires. For protection purposes, the strain gauges 940 and the electrical traces may be coated with a soft polymeric film, such as parylene or PDMS, a biocompatible epoxy, or a monolayer biomolecular coating. Alternatively, each strain gauge 940 could have an integral telemetry device constructed using MEMS and/or microelectronic fabrication techniques.

A metal tube 960 is attached, in a manner not shown, to the end cap 932 and extends into the interior chamber of the fusion cage 920. A pressure sensor, such as the pressure sensor 42 described above, is positioned inside the end of the tube 960 and coated with a dielectric gel as described above. Wires (not shown) extend through the tube 960 to electrically connect the pressure sensor to the telemetry device 950. The tube 960 containing the pressure sensor 42 may be packaged within a biomolecular coating or coated with thin layers of a soft biocompatible material, such as parylene or PDMS.

As shown in FIG. 18, the telemetry device 950 on the end cap 932 of the fusion cage 920 includes an electronics module 960 and an antenna 970. In the same manner as described above with regard to the previous embodiments, the telemetry device 950 is inductively powered by the readout/power supply unit 160 and is operable to transmit data from the strain gauges 940 and pressure sensor 42 via an RF carrier signal out to the readout/power supply unit.

The apparatus 910 according to the ninth embodiment of the present invention functions to provide a continuous or on-demand in vivo assessment of bony incorporation, and thus the fusion of the fusion cage 920 and the vertebrae 24 and 26, as well as the biomechanical performance of the fusion cage.

In addition to the telemetry schemes described above, it is contemplated that an alternative telemetry scheme using a tank circuit (not shown) could be employed with each of the aforementioned embodiments of the present invention. It is known that a change in capacitance or inductance on a sensor, such as a pressure sensor or a strain gauge, can be detected using a tank circuit. Such a tank circuit has either a variable capacitance and a fixed inductance, or a variable inductance and a fixed capacitance.

If the tank circuit has a variable capacitance, the capacitance will change as the pressure or strain, depending on the type of sensor, changes. This change in capacitance leads to changes in resonant frequency that can be detected. The capacitance changes can then be calculated using the following equation: $f_0=\frac{1}{2}\pi(LC)^{1/2}$, where L is the inductance and C is the capacitance. This same equation is also used to calculate inductance changes if the capacitance of the tank circuit is fixed. In the embodiments discussed above where there are multiple sensors, each sensor is designed to operate within a specific resonant frequency band. The tank circuit is then swept over range of frequencies so that the individual resonant frequency of each sensor, which corresponds to the output of each sensor, can be identified.

In the present invention, the tank circuit telemetry scheme could be employed in several different ways. The circuitry of the tank circuit could be added to the electronics module associated with each of the implanted sensors. Alternatively, the implanted sensors could be capacitive sensors having an integral tank circuitry. Finally, the conventional tank circuit described above (variable capacitance or variable inductance) could be configured such that the variable capacitor and one half of the inductor are fabricated on the same sensing diaphragm. The other half of the inductor is combined with a fixed electrode of the capacitor such that when the sensing diaphragm moves, the capacitance and the inductance increase or decrease together.

From the above description of the invention, those skilled in the art will perceive improvements, changes and modifications. For example, it is contemplated that the EMF signals exchanged between the readout/power supply unit and the transducer assemblies could be infrared transmissions rather than RF transmissions. Such improvements, changes and modifications within the skill of the art are intended to be covered by the appended claims.

Having described the invention, we claim:

1. An apparatus for providing an in vivo assessment of loads on adjacent bones in a living being, said apparatus comprising:

a body for insertion between the adjacent bones;

a first sensor assembly located within said body, said first sensor assembly generating an output signal in response to and indicative of a load being applied to said body through the adjacent bones; and at least one telemetric device, located outside of said body but within the living being, said at least one telemetric device being operable to receive said output signal from said first sensor assembly and to transmit an EMF signal dependent upon said output signal.

2. The apparatus of claim 1 wherein said first sensor assembly comprises a pressure sensor.

3. The apparatus of claim 1 further comprising a second sensor assembly located within said body, said at least one telemetric device being located at said second sensor assembly.

4. The apparatus of claim 3 wherein said second sensor assembly is operatively connected to said first sensor via a tube.

5. The apparatus of claim 3 wherein said first sensor assembly is maintained in physical communication with an interior surface of said body.

6. The apparatus of claim 1 further comprising an implant associated with the adjacent bones, said implant being external to said body.

7. The apparatus of claim 6 wherein said implant is connected to the adjacent bones to stabilize the adjacent bones.

8. The apparatus of claim 6 further comprising at least one strain gauge mounted on said implant, said at least one strain gauge for generating a second output signal in response to a load being applied to said implant, said at least one strain gauge being electrically connected with said at least one telemetric device.

9. The apparatus of claim 6 wherein said at least one telemetric device is located on said implant.

10. The apparatus of claim 9 wherein said at least one telemetric device is operatively connected to said first sensor via a tube such that said first sensor assembly is positioned inside a first end of said tube and a second end of said tube is attached to said implant.

11. The apparatus of claim 10 wherein said tube is packaged with a biomolecular coating such that said tube is covered with a monolayer coating of a desired biomolecule.

12. The apparatus of claim 11 wherein said the desired biomolecule comprises one of collagen and hyaluronan.

13. The apparatus of claim 1 wherein said body comprises a prosthetic device for preserving motion between the adjacent bones.

* * * * *